US010663449B2

(12) United States Patent
Evans et al.

(10) Patent No.: US 10,663,449 B2
(45) Date of Patent: May 26, 2020

(54) THIN FILM LIQUID THERMAL TESTING

(71) Applicants: Jonathan C. Evans, Midland, MI (US); Theodore W. Selby, Midland, MI (US); Marta Manning, Midland, MI (US); Gregory C. Miiller, Rhodes, MI (US); William John VanBergen, Coleman, MI (US)

(72) Inventors: Jonathan C. Evans, Midland, MI (US); Theodore W. Selby, Midland, MI (US); Marta Manning, Midland, MI (US); Gregory C. Miiller, Rhodes, MI (US); William John VanBergen, Coleman, MI (US)

(73) Assignee: TANNAS COMPANY, Midland, MI (US)

( * ) Notice: Subject to any disclaimer, the term of this patent is extended or adjusted under 35 U.S.C. 154(b) by 0 days.

(21) Appl. No.: 16/350,334

(22) Filed: Nov. 1, 2018

(65) Prior Publication Data
US 2019/0145948 A1 May 16, 2019

Related U.S. Application Data

(60) Provisional application No. 62/707,465, filed on Nov. 2, 2017.

(51) Int. Cl.
*G01N 33/28* (2006.01)
*B01J 10/02* (2006.01)

(52) U.S. Cl.
CPC ..... *G01N 33/2805* (2013.01); *G01N 33/2817* (2013.01); *B01J 10/02* (2013.01)

(58) Field of Classification Search
CPC .. G01N 33/2805; G01N 33/2817; B01J 10/02
See application file for complete search history.

(56) References Cited

U.S. PATENT DOCUMENTS

| 5,287,731 A | 2/1994 | Florkowski et al. |
| 5,401,661 A | 3/1995 | Florkowski et al. |
| D448,689 S | 10/2001 | Selby |
| 6,365,413 B1 | 4/2002 | Hall et al. |

OTHER PUBLICATIONS

ASTM D6335-09. "Standard test for determination of high temperature deposits by thermo-oxidation engine oil simulation test." 2009. (Year: 2009).*

(Continued)

*Primary Examiner* — Christopher Adam Hixson
(74) *Attorney, Agent, or Firm* — Christopher John Rudy

(57) ABSTRACT

Elevated temperature liquid testing apparatus and methodology in which a thin film of test liquid and a reactant/control gas are provided about the top of a depositor member that is surrounded by a special mantle, for example, a substantially cylindrically walled glass mantle. As an oxidative engine oil test, it may mimic turbocharger conditions of a modern internal combustion engine. For example, employing moist air, the apparatus can test a thin film of engine oil for oxidation deposits at a predetermined temperature, say, 285° C., 290° C., or cycled between 285° C. or 290° C. and 320° C. or 330° C.

21 Claims, 6 Drawing Sheets

(56) References Cited

OTHER PUBLICATIONS

ASTM International, ASTM D6335-18, "Standard Test Method for Determination of High Temperature Deposits by Therm-Oxidation Engine Oil Simulation Test," Jul. 2018.

ASTM International, ASTM D7097-16a, "Standard Test Method for Determination of High Temperature Piston Deposits by Thermo-Oxidation Engine Oil Simulation Test—TEOST MHT," Sep. 2016.

Evans et al., U.S. Appl. No. 62/707,465, filed Nov. 2, 2017 A.D., "Thin Film Liquid Thermal Testing."

Selby et al., U.S. Appl. No. 08/995,720, filed Dec. 22, 1997 A.D., "Thermo-Oxidation Engine Oil Simulation Test Apparatus and Method."

Selby et al., U.S. Appl. No. 09/059,132, filed Apr. 13, 1998 A.D., "Device for Measuring Heat Transmissibility of Oil."

Tannas Co., 2017, website materials printed Oct. 27, 2017 A.D., "TEOST Thermo-oxidation Engine Oil Simulation Test."

Tannas Co., 2017, online brochure printed Oct. 27, 2018 A.D., "TEOST Thermo-oxidation Engine Oil Simulation Test."

\* cited by examiner

THIN FILM LIQUID THERMAL TESTING

This claims benefits under 35 USC 119(e) of provisional patent application No. U.S. 62/707,465 filed on Nov. 2, 2017 A.D. The specification of that application, of course to include its drawings, is incorporated herein by reference.

FIELD AND PURVIEW OF THE INVENTION

This concerns elevated temperature liquid testing apparatus and methodology in which a thin film of test liquid and a reactant/control gas are provided about the top of a depositor member that is surrounded by a special mantle, for example, a substantially cylindrically walled glass mantle. As an oxidative engine oil test, it may mimic turbocharger conditions. For example, employing moist air, the apparatus can test a thin film of engine oil for oxidation deposits at a predetermined temperature, say, 285° C., 290° C., or cycled between 285° C. or 290° C. and 320° C. or 330° C.

BACKGROUND TO THE INVENTION

U.S. Pat. Nos. 5,287,731 and 5,401,661 to Florkowski et al. disclose thermo-oxidation engine oil simulation testing. In general, such testing mimics engine and turbocharger conditions in use at that time—for example, by maintaining test device reservoir oil at 95° C. and repeatedly flowing the oil over a test rod heated over a number of half hour cycles, each beginning at 150° C. (held one minute) then to 500° C. (held two minutes) and back to 150° C. (held twenty-four minutes)—with the test oil having an adversely affecting gas such as moist air and/or nitrous oxide pumped from the reservoir, up through a tube containing the heated test rod on which deposits form.

U.S. patent application Ser. No. 09/059,132 by Selby et al. discloses a device for measuring heat transmissibility of oil. In general, that device has a plurality of opposing thermocouples in a deposit formation assembly as in apparatus of the '731 and '661 patents to Florkowski et al.

The foregoing art employs flow from bottom to top, with 100-mL test sample sizes or larger. A commercial embodiment from that can be found as TEOST® apparatus, available from Tannas Company, Midland, Mich., further designated as "33C." Testing with TEOST® 33C apparatus is considered a bulk oil technique in simulation of conditions found in the turbocharger bearing area of an internal combustion engine. In commonly encountered practice, the reactor sump (reservoir pot) is held at 100° C. to form precursors at high-normal operating conditions; and cyclic heating of the deposit-inducing zone is carried out from 200° C. to 480° C. at designated intervals, say, every 9.5 minutes over 2½ hours or so, for example, over a 114-minute total test time, to simulate turbocharger deposit-forming conditions. A typical run may employ a ferric naphthanate catalyst and a 116-mL or so test sample. Compare, ASTM D6335.

U.S. patent application Ser. No. 08/995,720 by Selby et al. discloses a thermo-oxidation engine oil test apparatus and method. In general, such apparatus and method addresses milder conditions than turbocharger conditions, say, about from 100° C. to 200° C., with, however, test oil including adversely affecting gas such as moist air and/or nitrous oxide also being pumped from a reservoir, also in bulk flow, up through a tube containing a heated rod, on which deposits form.

U.S. Pat. No. 6,365,413 B1 to Hall et al. discloses a thin film thermal oxidative deposit testing device and method. In general, such testing employs a thin film of test oil that, within an enclosing tube, flows downward from an upper part of a central portion of a depositor surface, for example, a rod with a more narrow central portion having a helical wire wrapped around thereabout—noting in addition U.S. Pat. No. D448,689 S to Selby, which discloses a depositor rod for a thin film oxidative oil deposit testing device and method especially at moderately high temperature—with an adversely affecting gas such as moist air and/or nitrous oxide entering about a midpoint of the central portion. A reservoir pot may be avoided. Temperatures can be about from 200° C. to 400° C., with smaller sample sizes, say, about 8.5 mL, employed.

Commercial embodiments from the '413 patent may be found as TEOST® MHT® apparatus, also available from the Tannas Company. Testing with TEOST® MHT® apparatus is considered to be moderately high temperature testing of engine oil for evaluation of its performance correlated with the piston ring belt area of the engine, with the apparatus having a small, unheated storage volume that delivers a liquid sample to a single, thin-film heating zone with a wire-wound depositor rod held at 285° C. for twenty-four hours; a special bulbous clear glass mantle is provided for viewing of the depositor test area during testing; and volatized material can be separated and collected in a special adjunct vessel so that it may be further analyzed and investigated. Typically, a ferric naphthanate catalyst is employed with a 9.6-mL or so test sample. Compare, ASTM D7097.

As excellent as they are, however, and they excel indeed, the aforementioned bench testing apparatus and methodology are not without drawback or limitation, notably in light of the ever changing engine designs and formulations for engine oils, which would demand ever-more particular apparatus and methodology for accurate, precise, and reliable characterizations of their properties so that better, more efficient, and more reliable assessments and predictions can be made concerning their performance in the field. In particular, modern low viscosity oils, which can provide for better fuel efficiency and longer engine life, among other things, more and more contain chelated molybdenum compounds as additives, and these present special difficulties from deposits that can form, which are increased in number and varied in character. Moreover, modern internal combustion engines are designed to operate with lower turbocharger area temperatures than in former years, the modern engines typically operating between about 200° C. and 330° C. or so. Various samples of such modern oils may pass ASTM D6335 testing with TEOST® 33C apparatus, yet be proven to be a failing oil from automotive manufacturers' dynamometer turbocharger test assessments, and vice versa. The other historic TEOST® deposit test, i.e., ASTM D7097 testing with TEOST® MHT® apparatus, as mentioned above, is a ring belt deposit test, which was correlated with piston belt deposits of the Peugeot TU3MH engine test in contrast to the TEOST® 33C test that was correlated with both field oil and dynamometer turbocharger engine test data focusing on turbocharger galley bearing failure (at much higher temperatures that those of modern turbochargers). Although these two historic TEOST® tests do not correlate with each other, they were never intended to do so.

It would be desirable to ameliorate if not overcome one or more of the difficulties, drawbacks, and limitations of the prior art, and to improve the art. In particular, it would be desirable to provide more reliable test apparatus and methodology for testing engine oils for deposits under modern turbocharger conditions, notably to include modern engine oils with their additive packages, which may contain chelated molybdenum and/or other additive(s), and even extending to more advanced formulations, and the like. It would be desirable to provide the art an alternative.

A Full Disclosure of the Invention

Provided hereby is apparatus for testing liquid engine oil or other liquid as a test liquid for deposits formed at elevated temperatures under thin-film, reactant/control conditions, which comprises a heatable sample reservoir; a test liquid placement volume; in the test liquid placement volume, a heatable deposit-receiving surface in a form of a rod having a generally helical guide or channel for the test liquid such that a thin film can be formed thereon, in which bulk flow and its inherent difficulties in effective diffusion of a gaseous reactant/control substance into the test liquid can be avoided, and diffusion can be ameliorated or eliminated as a substantially limiting factor when the test liquid is delivered to the heatable deposit-receiving surface by a thin film forming unit, with the heatable deposit-receiving surface in liquid communication with the test liquid placement volume; the thin film forming unit, which can deliver the test liquid to the heatable deposit-receiving surface as the thin film; a reactant/control gas delivery unit; and a supply of at least one reactant/control gas, which may or may not adversely affect the test liquid—wherein the thin film forming unit and the reactant/control gas delivery unit are positioned in an upper reach of the test liquid placement volume so that both the liquid engine oil or other liquid as the test liquid, and the supply of at least one reactant/control gas can be delivered about an upper reach of the heatable deposit-receiving surface, optionally, in addition to or in lieu of which, being delivered to the test liquid away from the heatable deposit-receiving surface in the test liquid placement volume; and a surrounding mantle spaced apart from the heatable deposit-receiving surface a distance substantially non-varying from top to bottom with respect to the heatable deposit-receiving surface. Provided as well is a method for testing liquid engine oil or other liquid as a test liquid for deposits formed at elevated temperatures under thin-film conditions, which comprises steps, not necessarily conducted in series, as follows: providing the apparatus for testing the test liquid for deposits formed at elevated temperatures under thin-film conditions; providing the test liquid; heating the heatable deposit-receiving surface; delivering the test liquid and the supply of at least one reactant/control gas about an upper reach of the heatable deposit-receiving surface for a predetermined time under elevated temperature, thin-film conditions; and checking for and/or assaying any deposit on the heatable deposit-receiving surface.

The invention is useful in liquid testing, especially of engine oil.

By the invention, the art is improved in kind and provided an alternative; and one or more of the difficulties, drawbacks, and limitations of the prior art is or are ameliorated or overcome. More reliable test apparatus and methodology is provided for testing for deposits from engine oils, notably to include modern engine oils with their additive packages, which may contain chelated molybdenum and/or other additive(s), especially under modern internal combustion engine turbocharger operating conditions, More particularly, highly accurate, precise, and reliable characterizations of engine oil properties, particularly their propensity for forming turbocharger deposits can be extended to modern, low viscosity, chelated molybdenum containing engine oils, other advanced formulations, and so forth and the like. Thus, predictions can be made better, more efficiently, and more reliably concerning their performance in the field. Collection and measurement of volatiles, which in an engine oil may typically comprise up to about 13% of the oil by weight, can be avoided and not compromise test performance. Furthermore, in particular, in contrast to historical TEOST® 33C turbo deposit testing (ASTM D6335)—where oil is pumped up a simple deposit rod from the bottom, which is found to actually flood the rod and its casing, which results in uncertainty as to whether all of the oil within the casing does or does not come in contact with the rod as the oil is pushed up and then back to the reservoir, and by which modern engine oils form high levels of deposits—it is believed to be critical to expose test oil to the top of the heatable deposit-receiving surface, with maintenance of contact with the oil to the rod for a more extended period of time at temperature(s) and condition(s) more representative of those encountered in a modern internal combustion engine turbocharger area, which is provided, for example, by employment of a deposit rod with helically wound wire about a central portion whereof such as employed in TEOST® MHT® testing. Unlike TEOST® MHT® testing, however, in which a bulbous glass mantle and separation of volatiles is employed, the present surrounding mantle, for example, embodied as a hollow cylindrically walled glass mantle configured generally as a straight tube to be consistently close to the heatable deposit-receiving surface, say, the steel wire-wound deposit rod otherwise employed in the TEOST® MHT® testing, does not allow for separation of lower molecular weight fractions from the test liquid, for example, low molecular weight hydrocarbons and so forth from the test oil. Rather, the present surrounding mantle maintains any lower molecular weight vaporized fraction in close proximity to the heatable deposit-receiving surface. With the present surrounding mantle, the lower molecular weight fractions that may be in a vapor phase condense, for the most part, in a drain tube configured to accommodate this, on their way back to a test liquid reservoir, which advantageously is heated to, say, about from 90° C. to 110° C., for example, about 100° C. The invention is efficient to manufacture and operate, with operator error not compromised.

Numerous further advantages attend the invention.

The drawings form part of the specification hereof. As to the drawings, which are not necessarily drawn to scale, the following is briefly noted:

Figure 1:
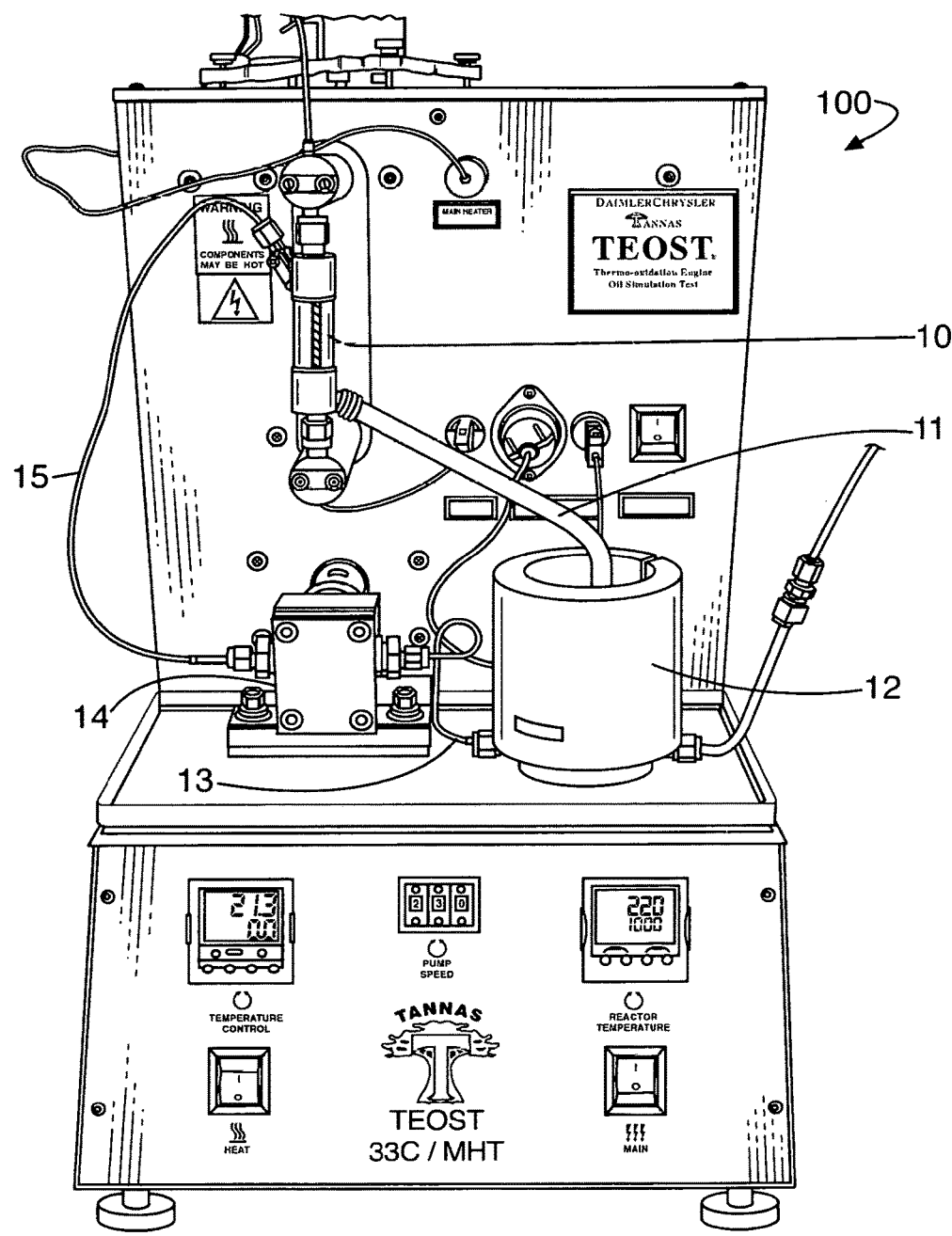
FIG. 1 is a front view of an apparatus hereof.
Figure 4A:
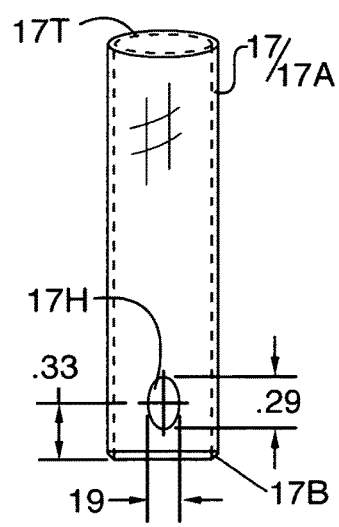
Figure 4B:
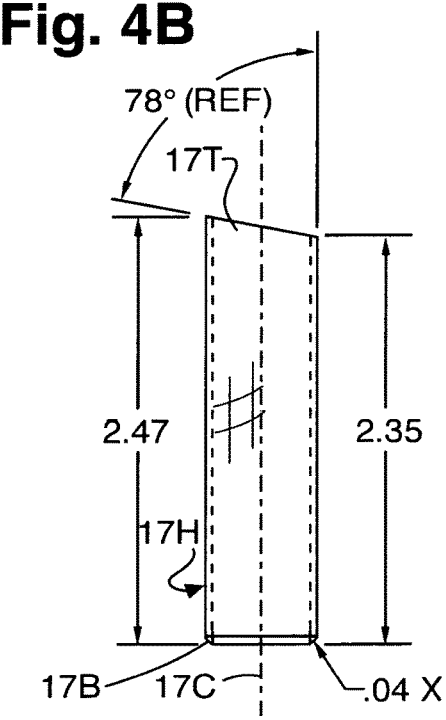
Figure 4C:
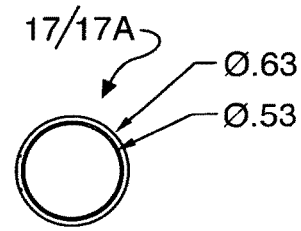
Figure 4D:
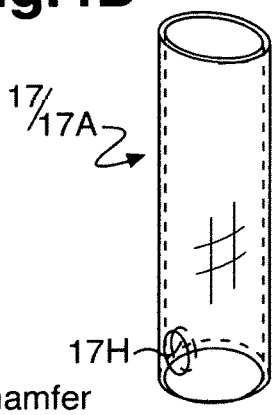

FIGS. 4A-4D are plan views of a glass mantle employed in the apparatus of FIG. 1, but inverted from the position it has when installed in that apparatus, with FIG. 4A a left side plan view in elevation (when considered upright in the apparatus); FIG. 4B a front plan view in elevation, which is orthogonal to the viewing direction of FIG. 4A (when considered upright in the apparatus); FIG. 4C a top plan view; and FIG. 4D a perspective plan view (taken, again, upside down). Unless otherwise noted or apparent, dimensions are in inches (1 in.=2.54 cm).

Figure 2:
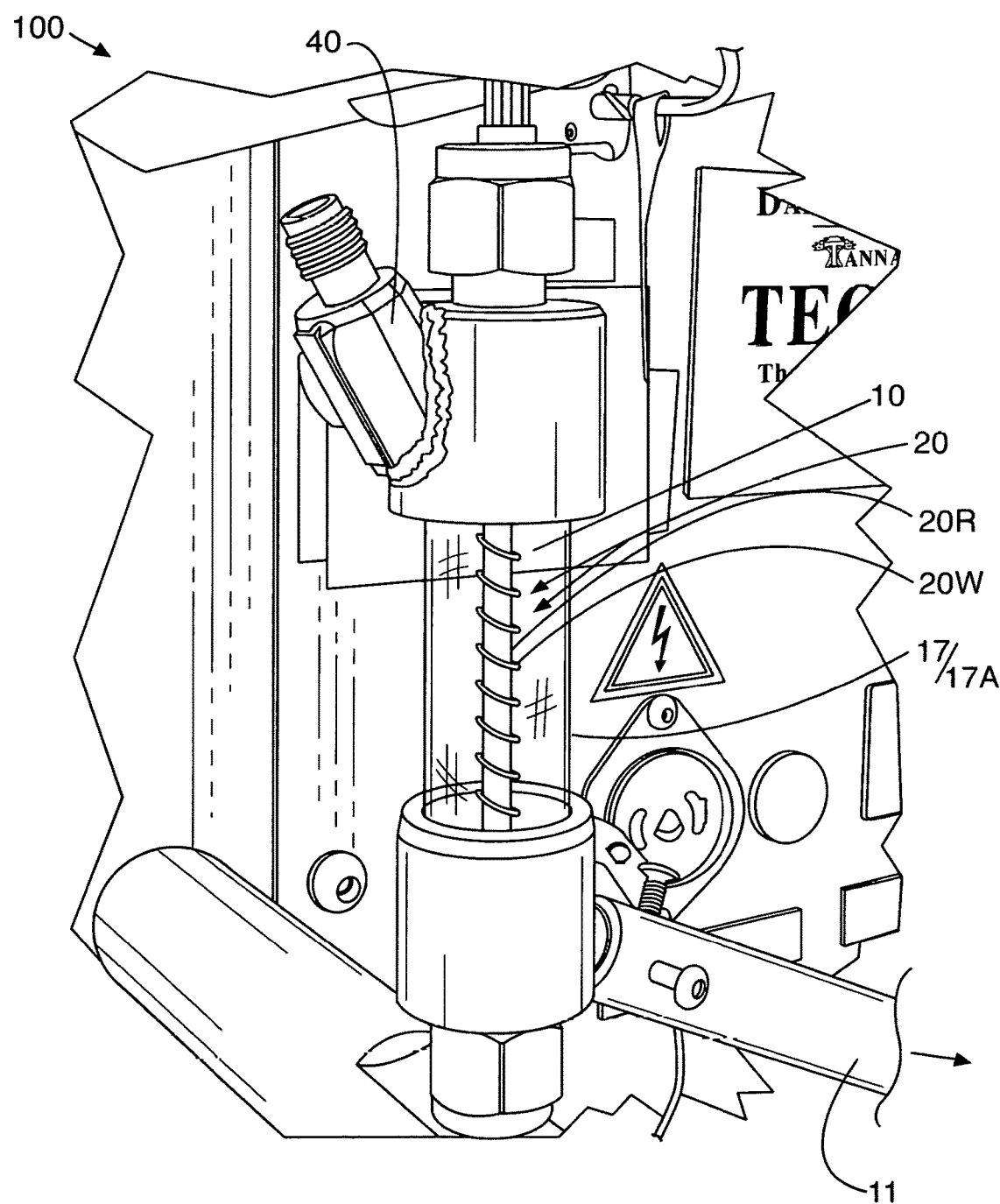
FIG. 2 is a front view of a portion of the apparatus of FIG. 1, focusing on its oleaginous liquid placement volume and pertinent parts therein and thereabout.
Figure 3:
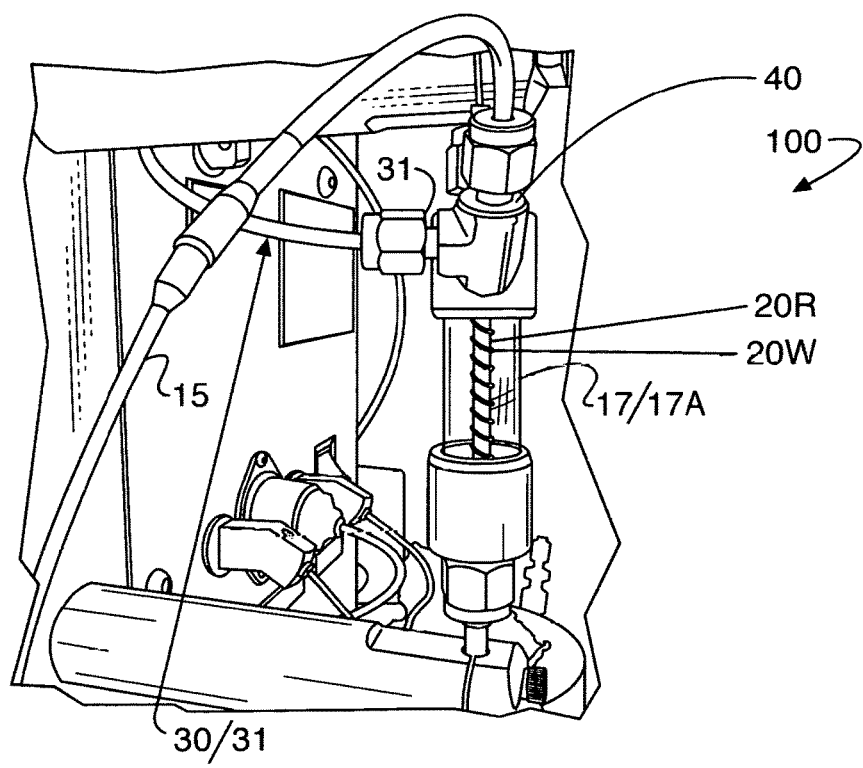
FIG. 3 is a side view of the portion of the apparatus, in general, in FIG. 2, noting its air inlet tube and fitting as an exemplary part of the oxidant gas delivery unit.
Figure 5A:
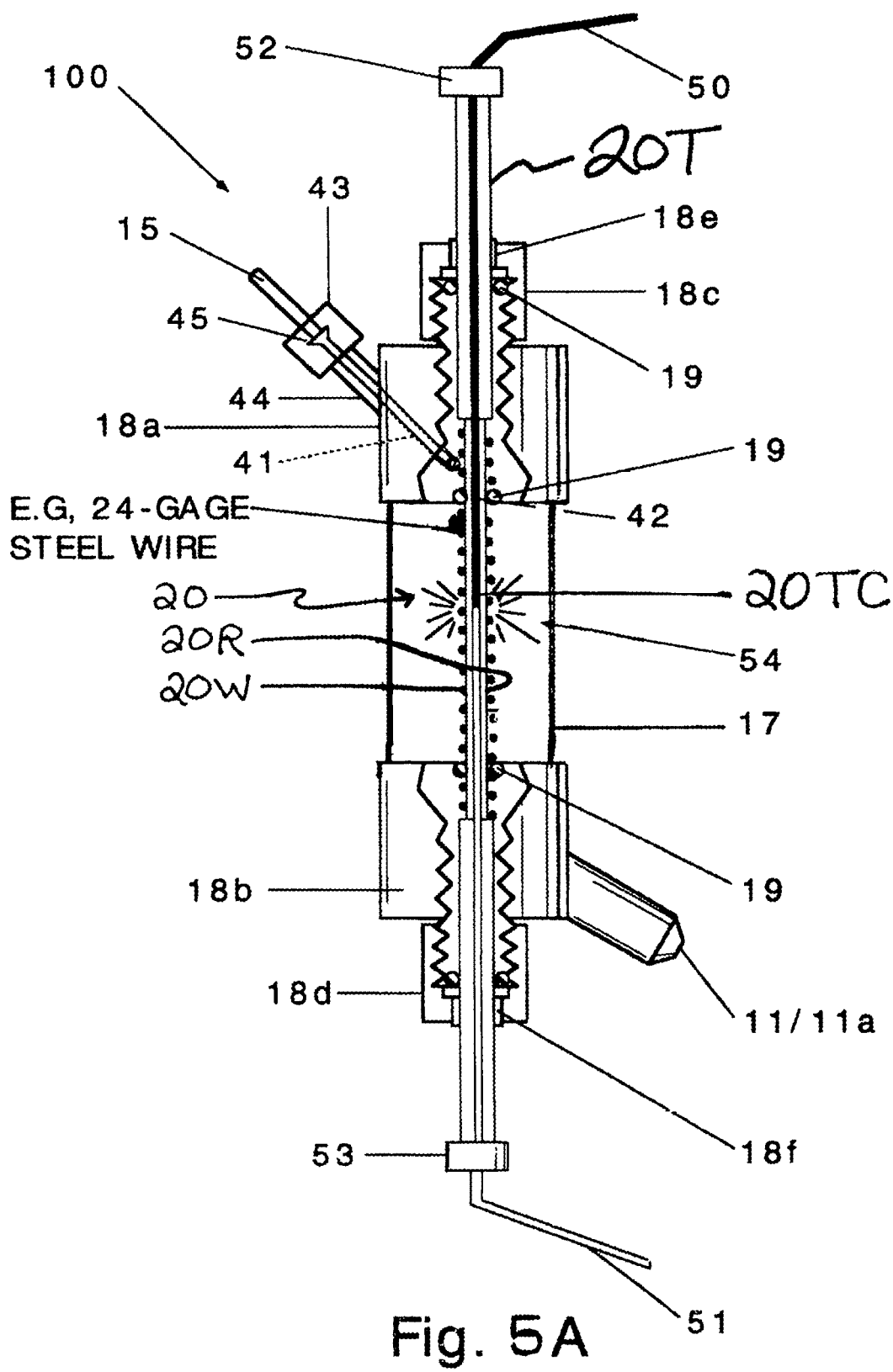
Figure 5B:
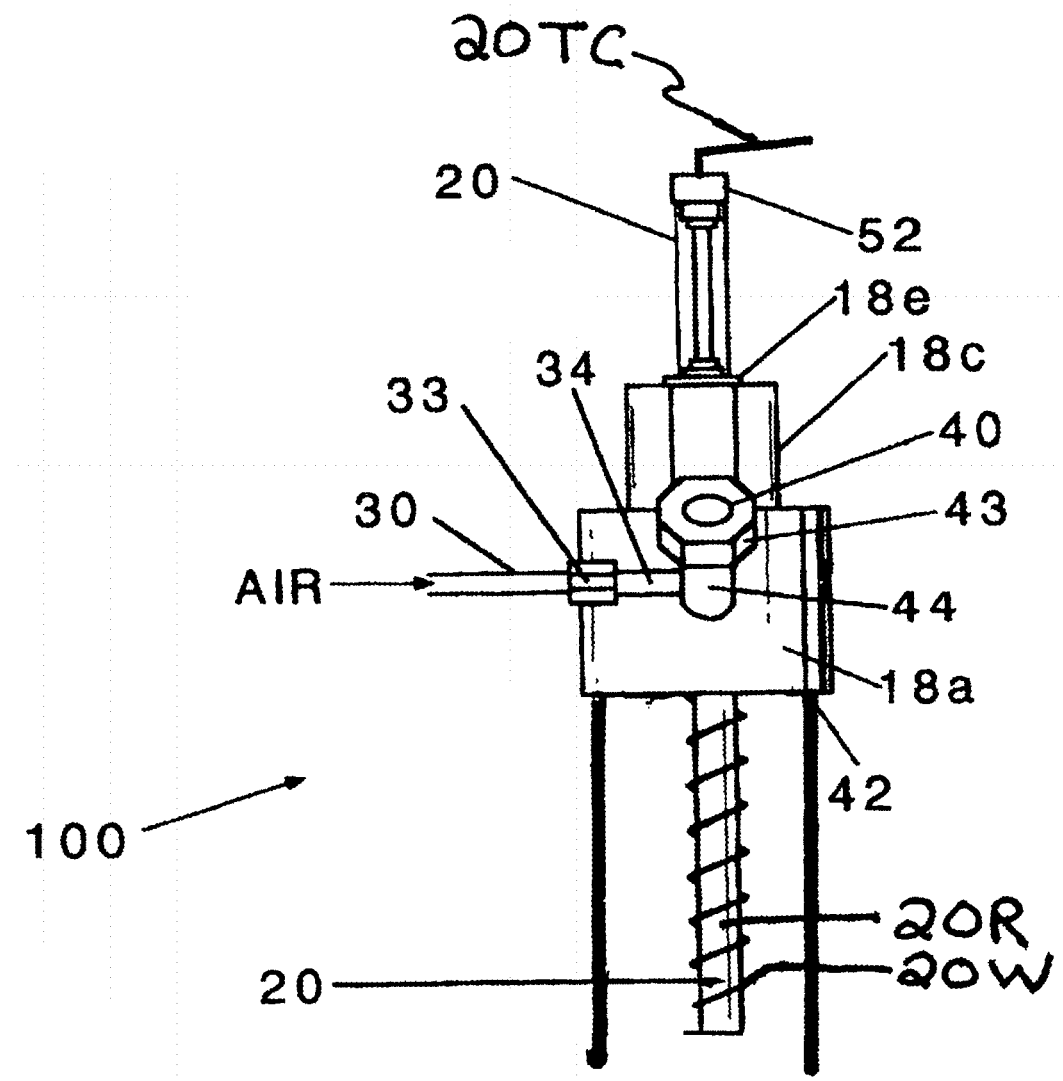

FIGS. 5A and 5B are plan/sectional views, each in elevation, of portions of the apparatus as depicted in FIG. 2, with FIG. 5A a front and FIG. 5B a side view.

Figure 6:
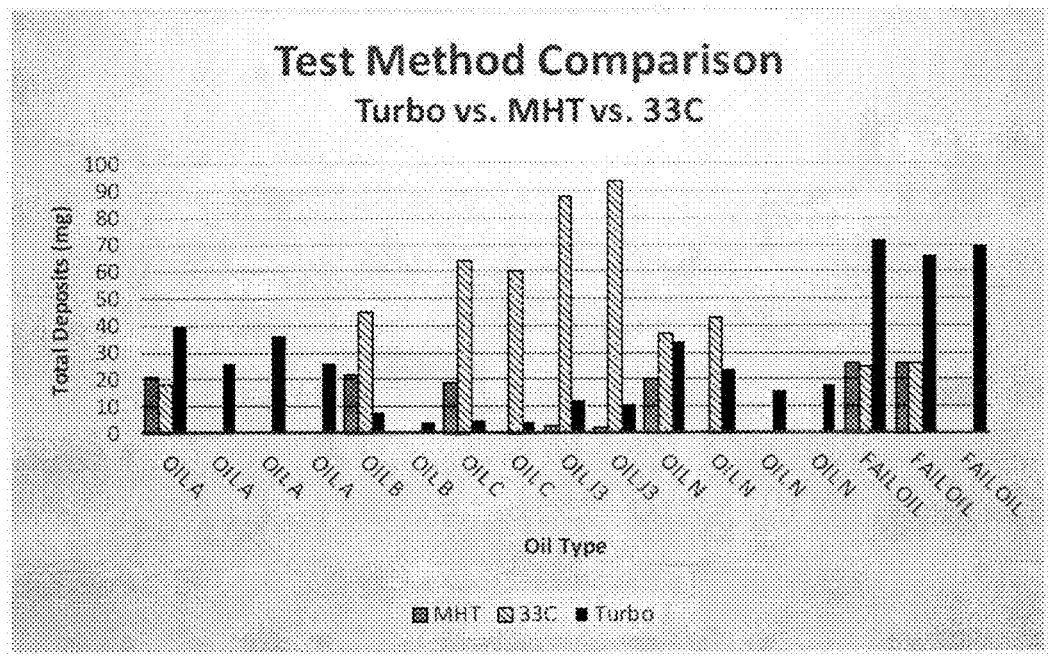

FIG. 6 is graph comparing thermo-oxidation testing of various engine oils.

Figure 7:
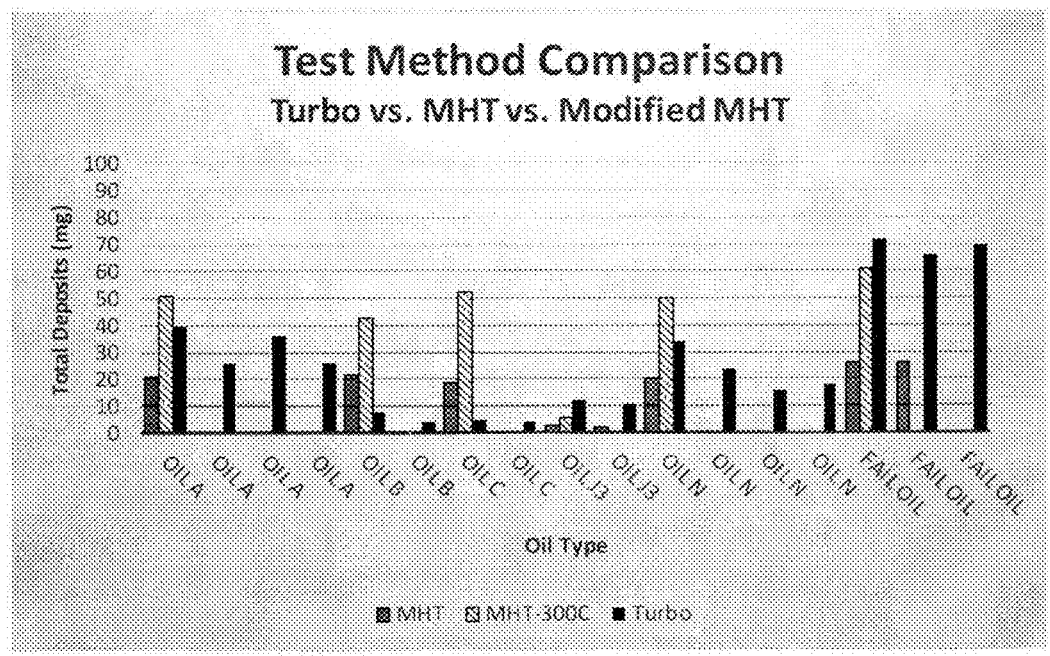

FIG. 7 is another graph comparing thermo-oxidation testing of various engine oils.

The invention can be further understood by the detail set forth below. As with the foregoing, the following, which also may be read in view of the drawings, is to be taken in an illustrative and not necessarily limiting sense.

The present apparatus can test liquid engine oil or other oleaginous liquid for deposits formed at elevated temperatures under thin-film, oxidation conditions, and the present method employs the apparatus. Compare, the cited '731 and '661 utility patents to Florkowski et al., the '132 utility patent application by Selby et al., the '720 utility patent application by Selby et al., the '413 patent to Hall et al., and the '689 design patent to Selby, and commercial embodiments.

With reference to the drawings, apparatus 100 includes test liquid placement volume 10, heatable deposit-receiving surface 20, supply 30 of at least one reactant/control substance, and thin film forming unit 40. Therewith, among other things, bulk flow and its inherent difficulties in effective diffusion of the reactant/control substance(s) especially into an oleaginous test liquid can be avoided, and diffusion can be ameliorated or eliminated as a substantially limiting factor.

The test liquid placement volume 10 may be serviced with return line 11, pot reservoir 12; first supply line 13; pump 14; and second supply line 15. These may be made of any suitable material, for example, stainless steel and/or glass. In addition to or in lieu of the pot reservoir 12, sample flow features such as the return line 11, first supply line 13, pump 14, and second supply line 15, any or all of which may be provided with a heater to heat the test liquid, may be considered to make up a heatable sample reservoir. Typically, however, the pot reservoir 12 is present and is provided with the primary, if not sole, heater to heat the test liquid. This heating keeps the test liquid heated at a predetermined level during its residence outside the test liquid placement volume 10. Defining in part the test liquid placement volume 10 is see-through wall 17, for example, made of a high-temperature glass such as VYCOR® or PYREX®, may be in the form of a substantially cylindrical hollow tube or mantle apparatus 17A which envelopes and allows visible observation of the heatable depositor-receiving surface 20. The mantle apparatus 17A can have beveled top 17B radially orthogonal to central axis 17C, upper hole 17H to allow entry of test liquid, for example, test oil, and bottom truncation 17T, which may have a non-orthogonal angle, say, from an about 65-degree to an about 85-degree angle with respect to the central axis 17C, with the non-orthogonal truncation for the purpose of directing flow drainage of the test liquid into the return line 11. The mantle apparatus 17C may be sealed by O-rings 19, for example, of VITON high-temperature elastomer material, to help insure that there is minimal or no loss of lower molecular weight fractions of the test sample. Provision is thus be made for employment of a small sample of test liquid, for example, an about 10-mL or typically an about 20-mL volume. The heated pot reservoir of the TEOST® 33C apparatus and of the '731 and '661 patents to Florkowski et al. can be beneficially employed with respect to a 20-mL sample of test liquid.

In the test liquid placement volume 10 and in liquid communication therewith is the heatable deposit-receiving surface 20—say, in a form of a rod 20R, for example, of stainless steel, which may be hollow to accommodate thermal heating element 20T, for example, an electrical resistance heating wire, and/or a heat-sensing thermocouple 20TC, and which has a generally helical guide or channel that may be provided by helically wound wire 20W such as of stainless steel—for contact with a test liquid. The heatable deposit-receiving surface 20, may be found in conjunction with an electrically resistive body as, for example, when in the form of the rod 20R, and be heated by passing electricity through the same.

Although the test liquid may be any suitable liquid, it is advantageously an oleaginous liquid, for example, a sample of an engine oil to include its additive package. The engine oil may be constituted for employment in a gasoline-powered and/or a diesel-powered internal combustion engine.

The supply 30 of at least one of at least one gaseous reactant/control substance, another substance that may adversely affect the test liquid, and an inert control substance, is provided, for example, through delivery unit 31 such as a tube through which can be delivered, as from pump action, dry or moist air, oxygen-enriched air, pure oxygen, oxygen-depleted air, ozone, nitrogen, carbon dioxide-enriched air, carbon dioxide, carbon monoxide, nitric oxide, nitrous oxide, sulfur trioxide, air containing a volatilized or vaporized organic compound or mixture such as hexane, benzene or gasoline, and argon and so forth. Other gaseous reactant/control substance(s) such as hydrogen peroxide, benzoyl peroxide, di-tert-butylperoxide, di-cumylperoxide, cumene hydroperoxide, tert-butylperoctoate, 2-ethylhexyl-nitrate, and so forth may be employed alone or in combination. For example, di-tert-butylperoxide can be employed in the test liquid, with air and nitric oxide being supplied separately around the heatable deposit-receiving surface 20. Delivery of the reactant/control substance may be at any suitable rate. For example, moist air may be delivered, say, at an about 0.1- to 15- or 20-mL per minute flow rate, to include an about 10-mL per minute flow rate, to the upper portion and interior of the mantle apparatus 17A without causing the entering moist air to bubble through the test liquid but rather causing it to enter through the reactant/control substance delivery unit 31. Alternatively, or in addition, one or more of such substances may be provided directly to the test liquid while it resides in a reservoir, a pump and/or a delivery line. Oxidation substance(s) and oxidizing conditions are beneficially employed. Advantageously, the reactant/control gas contains or releases oxygen.

A thin film of the test liquid can be formed on the heatable deposit surface 20 from delivery of the test liquid to the heatable deposit-receiving surface 20 by the thin film forming unit 40 including delivery tube 41 with an exit orifice close to the heatable deposit-receiving surface 20, for example again, the rod 20R with wound wire 20W, so that thereon the test liquid can form a thin film and flow down by gravity. The thin film produced may be about one thousandths of an inch. Any suitable rate of delivery and amount of the test liquid may be employed. For instance, an about 0.05- to 0.4-mL test liquid flow rate may be employed with an about 5- to 115- or 120-mL test liquid. For example, a first 10-mL aliquot of a 30-mL engine oil sample may be flushed through the apparatus 100 to cleanse it, followed by testing with a second 20-mL aliquot of the 30-mL sample, delivered at a flow rate of about 0.25 grams per minute. The lower flow rates provide for better residence time and potentially greater deposit formation.

Herein, the thin film forming unit 40 and the reactant/control gas delivery unit 31 are positioned in an upper reach of the test liquid placement volume so that both the test liquid and the supply of at least one reactant/control gas can be delivered about an upper reach of the heatable deposit surface 20. This has the advantages over the prior art as it enhances the formation of volatiles formed by low molecular weight hydrocarbons at operation temperature at the point of deposit formation on the surface of the heatable deposit-receiving surface 20.

Temperature of testing may vary. The temperature may be held constant or be varied, which may include by being cycled. For instance, referring to the heatable deposit-receiving surface 20, in testing engine oils, temperature(s) about from 250° C. to 400° C., to include about from 275° C. to 300° C. or 350° C. may be employed, say, about 285° C., about 290° C., or about from 285° C. or 290° C. to 320° C. or 330° C. then about from 320° C. or 330° C. to 290° C. in cycles. For example, again referring to the heatable deposit-receiving surface 20, the engine oil can be cycled for an hour through a step temperature increase of from 290° C. to 320° C. at the beginning of the hour, which can occur in minutes from heating, then held at 320° C. for 1.5 minutes, then decreased from 320° C. to 290° C., which also can occur or be caused to happen at an expeditious rate, and then held the temperature at 290° C. for the remainder of the hour.

Time of testing may vary. For instance, in testing engine oils, an about 1-hour to an about 60-hour test period may be employed, to include about 6-hour, 12-hour, 16-hour, 18-hour, 20-hour, 24-hour, 36-hour and 48-hour test periods, and periods bounded top or bottom by such times. A 6-hour to 24-hour period or longer may be employed for testing an engine oil designed for use in a gasoline-powered internal combustion engine, and a 36-hour to 48-hour period, more or less, may be employed for testing an engine oil designed for use in a diesel-powered internal combustion engine. An about from a 16-hour to 20-hour, for example, an about 18-hour, test period, say, using a constant set point of 290° C. or an hourly cycling temperature about from 290° C. to 320° C. and back, the first hour of which may be a constant 290° C., may provide for a heightened ability to distinguish pass/fail oils, for example, with an 18-hour total considered a standard, especially for oils designed for use in gasoline-powered internal combustion engines.

Weighing to assess deposit formation may be employed. Other tests may be applied, which may include infra-red spectroscopy, Raman spectroscopy, visible, ultra-violet and/or x-ray spectral analysis, scanning electron microscope (SEM) imaging, chemical analysis, and so forth. Also, residue oil can be analyzed at the end of testing to assess potential volatiles losses and/or chemical composition changes occurring during testing and deposit formation.

The examples set forth below further illustrate the invention.

REFERENCE OILS FOR THE EXAMPLES

Various reference oils are tested. The oils are fully formulated engine oils ranging from 5W-40 to 0W-20, with standard anti-wear/antioxidant zinc dithiophosphate (ZDDP) loadings of 700-800 ppm, molybdenum loadings ranging from 30-800 ppm, and calcium loadings ranging from 1200-2000 ppm. Some of these are oils are designated "passing oils" because they pass an automotive manufacture's dynamometer turbocharger engine test. A "failing oil" would fail that test. The passing oils, as determined by passing turbocharger engine testing of an automotive manufacturer, are designated as Oil J1, Oil J2, Oil A, Oil B, Oil C, and Oil N. The failing oil, as adjudged by the same test, is designated as "Fail Oil."

EXAMPLE 1

Apparatus as of FIG. 1 is used to test various reference engine oils on two separate apparatus by two separate groups, Savant R&D (SAV) and Tannas R&D (TAN). A PYREX® glass mantle as in FIGS. 4A-4D is employed with a commercially available TEOST® MHT® steel depositor rod having a steel spring helically wound around its midsection. Oil inlet is at the top of the rod. A ferric naphthenate catalyst (0.44 mg Fe/mL test oil—a 33C catalyst at MHT® test loading) is employed. Thermocouple depth is 9.7 cm. The thermocouple control placed at the desired "hot" spot on the rod, as established by a calibration method, from which the test temperature is maintained. Placing the thermocouple at a specific location ensures good temperature control at that location. The test temperature, which the thermocouple measures, is a constant 285° C., with moist air alone being employed at a 10-mL/minute flow rate. Moist air is used because it mimics normal humid air, which in an operational turbocharger is drawn in from the environment and used to boost combustion pressure in the piston cylinder and thus provide enhanced horsepower. The moist air is provided by bubbling purified air through clean water contained in a 25-mL Erlenmeyer flask. A 30-mL oil sample is employed, with a 10-mL aliquot being employed to flush lines of the apparatus and the remaining 20-mL aliquot being employed in the testing at a 25-g/minute flow rate for a 24-hour time. Results follow:

|  | Oil J1 | Oil J2 | Oil A | Oil C | Oil N | Fail Oil |
| --- | --- | --- | --- | --- | --- | --- |
| SAV | 46 mg | 18 mg | 72 mg |  | 64 mg | 98 mg |
| TAN | 52 mg | 23 mg | 71 mg | 18 mg |  | 85 mg. |

Good separation is observed between passing and failing oils. Although this is relative, and the industry determines what the specification is, i.e. what level of deposits is acceptable for a passing oil, a separation of 10-15 mg for passing and failing oils is found generally acceptable.

This shows that the present test apparatus and method are able to provide sufficient separation between the passing oil with the greatest amount of deposits, Oil A, and the reference failing oil, "Fail Oil" (20 mg). Also, it should be noted that the separation between a "passing" and a "failing" reference oil can be adjusted by varying the test temperature, test duration, catalyst loading, gas flow rate, pump speed, and so forth and the like.

EXAMPLE 2

Reference oils from the list set forth above for use in the examples are tested and benchmarked against standard TEOST® MHT® and TEOST® 33C tests for comparison. In addition to the oils employed in Example 1, another passing oil, Oil B, is employed.

The reference oils are tested according to the protocol of Example 1, excepting that an 18-hour run time (vs. the 24-hour run time of Example 1) and a temperature of 290° C. for the heatable depositor-receiving surface 20 is employed for the Turbo unit, i.e., for the configuration of the instant invention employed in the present example. For the TEOST® MHT® testing of the same reference oils, both employ only moist air as in Example 1, but otherwise are carried out according to ASTM D7097 and ASTM D6335 standard test methods, respectively. Results are depicted in FIG. 6.

This shows that ability to differentiate passing oils from failing oils is enhanced in comparison to the legacy tests. Results from the TEOST® MHT® testing lack the sensitivity of the Turbo test, as the differences in deposit levels vary only slightly between the passing and failing oils. Results from the TEOST® 33C testing yield higher deposit levels for some passing oils as compared to the failing oil, thus showing non-suitability for these formulations. The extent of separation is clearly differentiated from employment of the cylindrical, straight-walled glass mantle and other features of the instant invention (Turbo).

EXAMPLE 3

Additionally, reference oils are tested according to the protocol of Example 2. For comparison, those results are benchmarked against TEOST® MHT® testing as a control, and modified TEOST® MHT® testing at a higher temperature of 300° C., both using only the moist air as in Example 2 but otherwise per ASTM D7097. Results are depicted in FIG. 7.

This shows that deposit levels can be altered from temperature differences under TEOST® MHT® conditions. Also, it is noted that the TEOST® MHT® testing, even at 300° C., does not lead to the extent of separation of the instant invention (Turbo) at 290° C., as deposit levels tend to increase proportionately across all oil types as compared to the preferential separation from the instant invention (Turbo), which employs the cylindrical, straight-wall glass mantle and other features of the instant invention.

EPILOGUE

Overall, the present invention provides a laboratory test for evaluating the propensity of an oil to form automotive turbocharger deposits under modern turbocharger conditions verses expensive and time consuming automotive manufactures dynamometer turbocharger engine testing. Other liquids can be tested for deposits with the present invention.

Dramatic levels of separation in deposit levels between passing and failing oils can be obtained with the present invention.

In contrast with prior art, the present invention can provide notable improvement if not excel. For example, the MHT® test, which was not intended to simulate turbocharger conditions although engine modifications have reduced turbocharger temperatures closer to its operating parameters, when applied to advanced oils, in general, does not have sufficient sensitivity to be employed for turbocharger-condition assessment. The 33C test, which was originally designed for assessments related to turbochargers that operated at higher temperatures, is also not suitable for use in evaluating engine oils for current engines owing to interaction with some additive components, for example, chelated molybdenum, at elevated temperatures. The present invention addresses these shortcomings, and yields good correlation. Maintaining reservoir temperature, the capture of volatile component(s) and/or a selected temperature profile may be significant factor(s) in in providing for excelling performance. Other significant factor(s) may include the place of introduction of the test fluid into the apparatus, the rate of flow of test fluid over the rod, the amount of test fluid volatilized, and employment of the cylindrical, straight-wall glass mantle and other features of the instant invention.

Numerical values herein may be taken in an approximate or exact sense.

INCORPORATIONS BY REFERENCE

The aforementioned patents and patent applications—U.S. Pat. Nos. 5,287,731 and 5,401,661; U.S. patent application Ser. Nos. 09/059,132 and 08/995,720; and U.S. Pat. No. 6,635,413 B1 and D448,689 S—are incorporated herein by reference.

CONCLUSION TO THE INVENTION

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous and sundry adaptations can be effected within its spirit, the literal claim scope of which is particularly pointed out by the following claims:

What is claimed is:

1. An apparatus for testing liquid engine oil or other liquid as a test liquid for deposits formed at elevated temperatures under thin-film, reactant/control conditions, which comprises a heatable sample reservoir; a test liquid placement volume; in the test liquid placement volume, a heatable deposit-receiving surface in a form of a rod having a generally helical guide or channel for the test liquid such that a thin film can be formed thereon, in which bulk flow and its inherent difficulties in effective diffusion of a gaseous reactant/control substance into the test liquid can be avoided, and diffusion can be ameliorated or eliminated as a substantially limiting factor when the test liquid is delivered to the heatable deposit-receiving surface by a thin film forming unit, with the heatable deposit-receiving surface in liquid communication with the test liquid placement volume; the thin film forming unit, which can deliver the test liquid to the heatable deposit-receiving surface as the thin film; a surrounding mantle spaced apart from the heatable deposit-receiving surface a distance substantially non-varying from top to bottom with respect to the heatable deposit-receiving surface, and forming in part a boundary to the test liquid placement volume; a drain tube configured to communicate with the test liquid placement volume and the heatable sample reservoir; a reactant/control gas delivery unit; and a supply of at least one reactant/control gas, which may or may not adversely affect the test liquid—wherein the thin film forming unit and the reactant/control gas delivery unit are positioned in an upper reach of the test liquid placement volume so that both the liquid engine oil or other liquid as the test liquid, and the supply of at least one reactant/control gas, can be delivered about an upper reach of the heatable deposit-receiving surface; and the surrounding mantle is configured to maintain any lower molecule weight vaporized fraction of the test liquid in close proximity to the heatable deposit-receiving surface, and the drain tube is configured to condense for the most part said any lower weight vaporized fraction and to return the same to the heatable sample reservoir, such that separation of said any lower molecular weight fraction from the test liquid substantially does not occur during operation of the apparatus.

2. The apparatus of claim 1, wherein, in addition to or in lieu of the capability of the supply of at least one reactant/control gas being delivered about an upper reach of the heatable deposit-receiving surface, the supply of at least one reactant/control gas can be delivered to the test liquid away from the heatable deposit-receiving surface in the test liquid placement volume.

3. The apparatus of claim 1, wherein test liquid placement volume includes a boundary provided by a glass mantle including a see-through wall made of a high-temperature glass in a form of a substantially cylindrical hollow tube about a central axis, said tube having a beveled top radially orthogonal to the central axis, an upper hole to allow entry of a test liquid, and a bottom truncation for the purpose of directing flow drainage of the test liquid, said bottom truncation having a non-orthogonal angle.

4. The apparatus of claim 2, wherein test liquid placement volume includes a boundary provided by a glass mantle including a see-through wall made of a high-temperature glass in a form of a substantially cylindrical hollow tube about a central axis, said tube having a beveled top radially orthogonal to the central axis, an upper hole to allow entry of a test liquid, and a bottom truncation for the purpose of directing flow drainage of the test liquid, said bottom truncation having a non-orthogonal angle.

5. A glass mantle for an apparatus for testing liquid engine oil or other liquid as a test liquid for deposits formed at elevated temperatures under thin-film, reactant/control conditions, which has a test liquid placement volume, said glass mantle comprising a see-through wall made of a high-temperature glass in a form of a substantially cylindrical hollow tube about a central axis, said tube having a beveled top radially orthogonal to the central axis, an upper hole to allow entry of a test liquid, and a bottom truncation for the purpose of directing flow drainage of the test liquid, said bottom truncation having a non-orthogonal angle.

6. The glass mantle of claim 5, wherein the non-orthogonal angle is about from 65 to 85 degrees with respect to the central axis.

7. A method for testing liquid engine oil or other liquid as a test liquid for deposits formed at elevated temperatures under thin-film conditions, which comprises steps, not necessarily conducted in series, as follows:
providing an apparatus for testing the test liquid for deposits formed at elevated temperatures under thin-film conditions, which includes a heatable sample reservoir; a test liquid placement volume; in the test liquid placement volume, a heatable deposit-receiving surface in a form of a rod having a generally helical guide or channel for the test liquid such that a thin film can be formed thereon, in which bulk flow and its inherent difficulties in effective diffusion of a gaseous reactant/control substance into the test liquid can be avoided, and diffusion can be ameliorated or eliminated as a substantially limiting factor when the test liquid is delivered to the heatable deposit-receiving surface by a thin film forming unit, with the heatable deposit-receiving surface in liquid communication with the test liquid placement volume; the thin film forming unit, which can deliver the test liquid to the heatable deposit-receiving surface as the thin film; a surrounding mantle spaced apart from the heatable deposit-receiving surface a distance substantially non-varying from top to bottom with respect to the heatable deposit-receiving surface, and forming in part a boundary to the test liquid placement volume; a drain tube configured to communicate with the test liquid placement volume and the heatable sample reservoir; a reactant/control gas delivery unit; and a supply of at least one reactant/control gas, which may or may not adversely affect the test liquid—wherein the thin film forming unit and the reactant/control gas delivery unit are positioned in an upper reach of the test liquid placement volume so that both the liquid engine oil or other liquid as the test liquid, and the supply of at least one reactant/control gas, can be, and are, delivered about an upper reach of the heatable deposit-receiving surface; and the surrounding mantle is configured to maintain any lower molecule weight vaporized fraction of the test liquid in close proximity to the heatable deposit-receiving surface, and the drain tube is configured to condense for the most part said any lower molecular weight vaporized fraction and to return the same to the heatable reservoir, such that separation of said any lower molecular weight fraction from the test liquid substantially does not occur during operation of the apparatus;
providing the test liquid, and heating it or maintaining its heat at a first temperature in the heatable sample reservoir;
heating the heatable deposit-receiving surface to a second temperature;
delivering the test liquid and the supply of at least one reactant/control gas about an upper reach of the heatable deposit-receiving surface for a predetermined time under elevated temperature, thin-film conditions at or about the second temperature;
maintaining said any lower molecular weight vaporized fraction in close proximity to the heatable deposit-receiving surface with employment of the surrounding mantle, and condensing said any lower weight vaporized fraction and returning the same to the heatable sample reservoir with employment of the drain tube, such that separation of said any lower molecular weight fraction from the test liquid substantially does not occur during operation of the apparatus; and
checking for and/or assaying any deposit on the heatable deposit-receiving surface.

8. The method of claim 7, wherein the test liquid is an oleaginous liquid; the first temperature is about from 90° C. to 110° C.; the second temperature is about from 250° C. to 400° C., and the predetermined time is about from 1 to 60 hours.

9. The method of claim 8, wherein the second temperature is held constant about from 275° C. to 300° C., and the predetermined time is about from 12 to 48 hours.

10. The method of claim 9, wherein the second temperature is about 290° C., and the predetermined time is about from 16 to 20 hours.

11. The method of claim 8, wherein heating in the test liquid placement volume is cycled from about 275° C. to about 330° C. and back, and the predetermined time is about from 12 to 48 hours.

12. The method of claim 11, wherein the reactant/control gas is moist air, heating in the test liquid placement volume is cycled from about 290° C. to about 320° C. and back, and the predetermined time is about from 16 to 20 hours.

13. The method of claim 7, wherein the test liquid is an engine oil.

14. The method of claim 8, wherein the oleaginous liquid is an engine oil.

15. The method of claim 9, wherein the oleaginous liquid is an engine oil.

16. The method of claim 10, wherein the oleaginous liquid is an engine oil.

17. The method of claim 11, wherein the oleaginous liquid is an engine oil.

18. The method of claim 12, wherein the oleaginous liquid is an engine oil.

19. The method of claim 7, wherein, in addition to or in lieu of the capability of the supply of at least one reactant/control gas being delivered about an upper reach of the heatable deposit-receiving surface, the supply of at least one reactant/control gas can be, and is, delivered to the test liquid away from the heatable deposit-receiving surface in the test liquid placement volume.

20. A method for testing liquid engine oil or other liquid as a test liquid for deposits formed at elevated temperatures under thin-film conditions, which comprises steps, not necessarily conducted in series, as follows:

provinding an apparatus for testing the test liquid for deposits formed at elevated temperatures under thin-film conditions, which includes a heatable sample reservoir; a test liquid placement volume; in the test liquid placement volume, a heatable deposit-receiving surface in a form of a rod having a generally helical guide or channel for the test liquid such that a thin film can be formed thereon, in which bulk flow and its inherent difficulties in effective diffusion of a gaseous reactant/control substance into the test liquid can be avoided, and diffusion can be ameliorated or eliminated as a substantially limiting factor when the test liquid is delivered to the heatable deposit-receiving surface by a thin film forming unit, with the heatable deposit-receiving surface in liquid communication with the test liquid placement volume; the thin film forming unit, which can deliver the test liquid to the heatable deposit-receiving surface as the thin film; a surrounding mantle spaced apart from the heatable deposit-receiving surface a distance substantially non-varying from top to bottom with respect to the heatable deposit-receiving surface, wherein the surrounding mantle includes a see-through wall made of a high-temperature glass in a form of a substantially cylindrical hollow tube about a central axis, said tube having:

a beveled top radially orthogonal to the central axis;

an upper hole to allow entry of a test liquid; and a bottom truncation for the purpose of directing flow drainage of the test liquid, said bottom truncation having a non-orthogonal angle with respect to the central axis;

a reactant/control gas delivery unit; and a supply of at least one reactant/control gas, which may or may not adversely affect the test liquid—wherein the thin film forming unit and the reactant/control gas delivery unit are positioned in an upper reach of the test liquid placement volume so that both the liquid engine oil or other liquid as the test liquid, and the supply of at least one reactant/control gas, can be delivered about an upper reach of the heatable deposit-receiving surface;

providing the test liquid, and heating it or maintaining its heat at a first temperature in the heatable sample reservoir;

heating the heatable deposit-receiving surface to a second temperature;

delivering the test liquid and the supply of at least one reactant/control gas about an upper reach of the heatable deposit-receiving surface for a predetermined time under elevated temperature, thin-film conditions at or about the second temperature; and checking for and/or assaying any deposit on the heatable deposit-receiving surface.

21. The method of claim 20, wherein the non-orthogonal angle in the surrounding mantle is about from 65 to 85 degrees with respect to the central axis.

* * * * *